April 26, 1938. F. C. STIELOW Plant Pat. 277
WHITE ROSE
Filed May 24, 1937
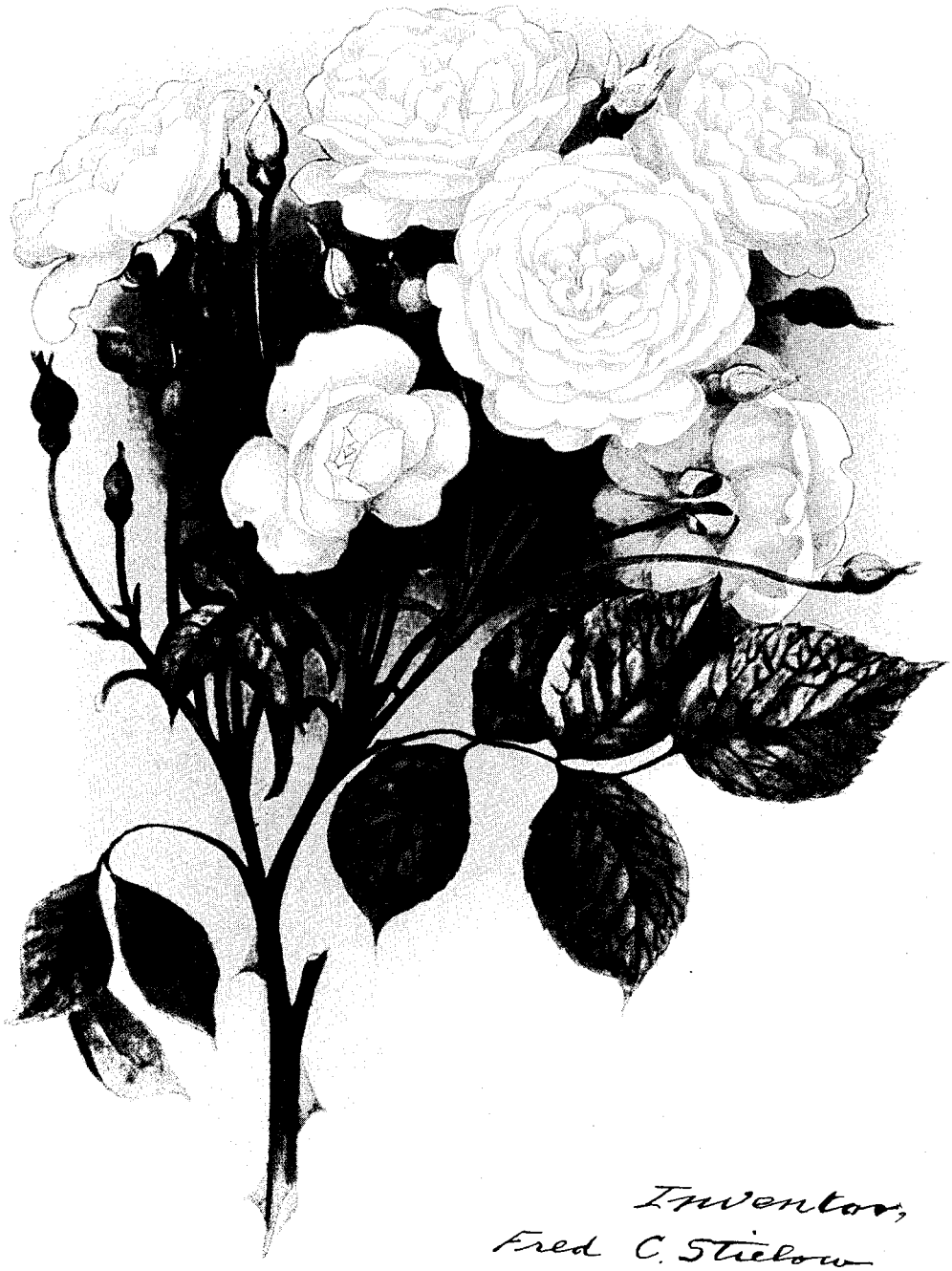
Inventor,
Fred C. Stielow
by
Rummler, Rummler
& Woodworth, Attys
Addison E. Avery Patented Apr. 26, 1938

Plant Pat. 277

UNITED STATES PATENT OFFICE

277

WHITE ROSE

Fred C. Stielow, Niles Center, Ill.

Application May 24, 1937, Serial No. 144,468

1 Claim. (Cl. 47—61)

The new variety of white rose herein described and illustrated is a sport of an Australian rose known in the United States as "Mrs. Finch", the botanical name of which is unknown to me.

The parent plant, which bears a light pink rose, was purchased from A. N. Pierson, Inc., of Cromwell, Conn., and the mutant thereof which bore white roses was carefully propagated in my greenhouses in Niles Center, Illinois, for a year and a half, until I have succeeded in making permanent the desirable variations.

The new rose is distinguishable from that of the parent plant mainly in the blossoms which turn very white when fully open and are more double and cup-shaped than the blossoms of the "Mrs. Finch". The new plant grows vigorously, blossoms freely and continuously and the cut flower has long-lasting qualities. The petals do not fall off. The plant has been produced in quantity by budding and grafting for about a year and a half and remains true to form and color and free from disease.

The accompanying illustration shows in full color a typical spray of the plant as having numerous buds, some of which are partly open and others in full bloom.

A partly opened flower is less white than when fully open when the light pink on the tips of the petals gradually becomes white.

Prominent features of this rose are found in the color of the blossoms, its unusual quantity of bloom produced continuously and its keeping qualities, and like "Mrs. Finch" is used to a considerable extent in making up corsage bouquets. The new plant has been asexually reproduced and the distinct characteristics described are maintained true to form and appear to be permanently fixed. When fully open, the outer whorls of petals are white with a waxy texture.

The colors of this rose in detail and with exactness are as follows, reference being made to Maerz & Paul's Color Dictionary:

*Main blossom*

| Section | Plate | Letter | No. |
|---|---|---|---|
| Main petals | 10 | A | 1 |
| Shadow tones at base of and between petals | 17 | F | 2 |
| Section at base of center | 17 | I | 1 |

*Buds*

| | | | |
|---|---|---|---|
| Edge of center of larger buds | 1 | G | 1 |
| General tone of buds darker than open flowers | 17 | D | 2 |
| Outside of petals in small unopened buds | 17 | J | 3 |

*Leaves*

| Section | Plate | Letter | No. |
|---|---|---|---|
| Large leaves with the veins very pronounced | 20 | L | 7 |
| Being outlines in giving a honeycomb or network effect | 22 | L | 9 |

*Stems*

| | | | |
|---|---|---|---|
| Stems | 21 | L | 9 |

*Thorns*

| | | | |
|---|---|---|---|
| Thorns very large | 22 | K | 1 (page 66) |

The blossoms are borne in clusters, as on the parent rose, "Mrs. Finch", on strong, upright stems. They are cup-shaped and substantially two inches in width, with a petalage averaging 26 to 30 in number. The blossoms are mildly fragrant and when cut with fair care do not wither on the stems for substantially two weeks.

The bud averages two inches in length and when tightly closed, the inner petals, which form the peak of the bud, are a delicate shade of pink 1—G—1. The bud is also cup-shaped. The opening bud is not white but gradually turns white upon unfolding.

Toward the base of the peduncle, there are a number of leaf branches, but this plant is not nearly so bushy as the parent plant. The veins on the developed leaves are a very deep green 22—L—9 and branched which gives them a distinctive, network appearance. The stems contain some thorns toward the base which are hook-shaped.

The following is a detailed description of the rose plant and flower:

Parentage: Sport of "Mrs. Finch".

*Bloom*

*Color.*—10—A—1.
*Size.*—2 inches.
*Borne.*—In clusters like "Mrs. Finch".
*Form.*—More cup-shaped, more open and more double than "Mrs. Finch".
*Petalage.*—26 to 30.
*Blooms.*—All the year round.
*Lasting qualities.*—Very good.

*Bud*

*Form.*—Cup-shaped.
*Size.*—2 inches.

*Plant*

*Form.*—Bush.
*Growth.*—About 3 feet high.
*Foliage:*—
*Quantity.*—Less foliage than "Mrs Finch"—not so bushy.
*Color.*—20—L—7.
*Stems.*—As strong as "Mrs. Finch".
*Thorns.*—Hook-shaped.
Resists diseases prevalent among roses.

This now variety of rose is easily distinguished from the parent rose by its unusual waxy white color, by the blossoms being more double and more open, and by the number, size and keeping qualities of its blossoms.

I claim:

The herein disclosed rose, a sport from the "Mrs. Finch" and similar thereto in habits of growth and in having numerous buds; and definitely distinguishable therefrom by the waxy whiteness of the full, open bloom and the more cup-shaped form and doubleness of the bloom, and a more open or less bushy character of the plant.

FRED C. STIELOW.